United States Patent
Verkaart

(10) Patent No.: US 6,939,329 B1
(45) Date of Patent: Sep. 6, 2005

(54) APPARATUS FOR HOLDING AND OPERATING ONE OR MORE SYRINGES

(75) Inventor: Wesley H. Verkaart, Duxbury, MA (US)

(73) Assignee: Harvest Technologies Corporation, Plymouth, MA (US)

( * ) Notice: Subject to any disclaimer, the term of this patent is extended or adjusted under 35 U.S.C. 154(b) by 0 days.

(21) Appl. No.: 09/857,142

(22) PCT Filed: Oct. 6, 2000

(86) PCT No.: PCT/US00/26243

§ 371 (c)(1),
(2), (4) Date: Jun. 1, 2001

(87) PCT Pub. No.: WO01/26712

PCT Pub. Date: Apr. 19, 2001

Related U.S. Application Data

(60) Provisional application No. 60/158,302, filed on Oct. 8, 1999.

(51) Int. Cl.$^7$ .......................... A61M 1/06; A61M 37/00; A61M 5/00
(52) U.S. Cl. ........................... 604/191; 604/73; 604/82
(58) Field of Search ............................. 604/181, 187, 604/191, 173, 68, 71, 73, 82, 83, 218, 227; 222/134–137

(56) References Cited

U.S. PATENT DOCUMENTS

| | | | |
|---|---|---|---|
| 3,016,897 A | 1/1962 | Kendrick | |
| 4,979,942 A | 12/1990 | Wolf et al. | |
| 5,115,816 A | * 5/1992 | Lee | ............................ 600/562 |
| 5,179,983 A | 1/1993 | Cordner, Jr. et al. | |
| 5,290,259 A | 3/1994 | Fischer | |
| 5,395,326 A | 3/1995 | Haber et al. | |
| 5,582,596 A | 12/1996 | Fukunaga et al. | |

FOREIGN PATENT DOCUMENTS

| | | |
|---|---|---|
| CN | 2096371 | 2/1992 |
| EP | 0 538 174 A1 | 4/1993 |
| WO | WO 98/40115 | 9/1998 |

* cited by examiner

Primary Examiner—Michael J. Hayes
(74) Attorney, Agent, or Firm—Clark & Brody

(57) ABSTRACT

Apparatus for supporting a syringe (6, 10) includes a handle portion (2) and a cradle (4). A clip (14) is provided for connecting the plungers (8) of two or more syringes (6, 10), and two or more syringes (6, 10) are operated by placing one (6) in the cradle (4) and attaching the clip (14) to the plungers (8) for simultaneous operation of the plungers (8). The handle portion (2) also forms a cavity for storing the clips (14). The apparatus is preferably used in combination with an applicator tip (12) that combines the outputs from the two or more syringes (6, 10).

8 Claims, 2 Drawing Sheets

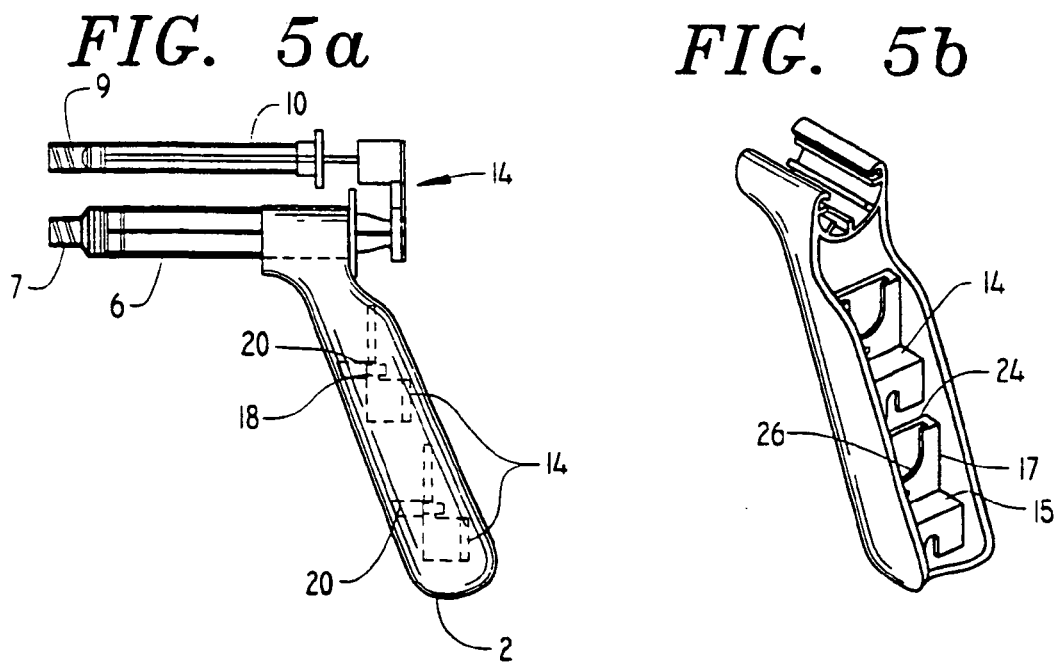
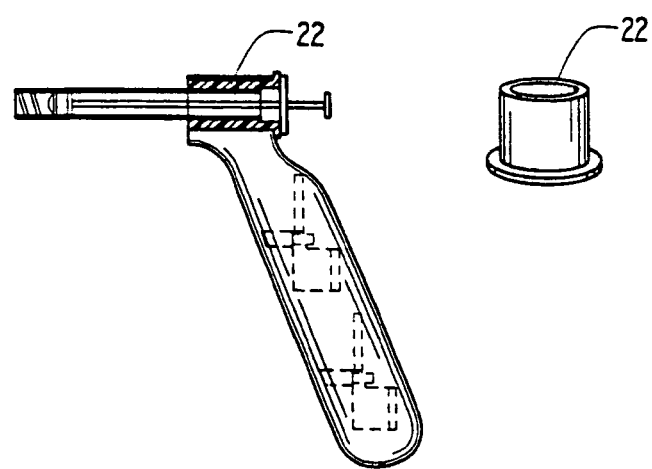

APPARATUS FOR HOLDING AND OPERATING ONE OR MORE SYRINGES

The application claims the benefit of Provisional Application No. 60/158,302, filed Oct. 8, 1999.

TECHNICAL FIELD

This invention relates to syringes. In particular, the invention relates to a device for holding one or more syringes to facilitate operation of a single syringe or to operate and combine the fluids from a plurality of syringes.

BACKGROUND ART

The operation of a syringe is well known. In a common use, a hypodermic needle is attached to the barrel of a syringe for injecting a fluid into a patient. Syringes also have other uses, such as the application of a fluid to an exterior surface or the injection of a fluid into a conduit.

It is also known to combine the fluids from two separate syringes for application of the mixture to an object. An example of this is the combination of a first fluid containing fibrinogen in a first syringe and a second fluid containing thrombin in a second syringe to provide a fibrin sealant. This type of syringe typically provides a combining tip having two inlets, each of which receives the outlet of a respective one of two syringes. The combining tip provides a Y-type channel for combining the two fluids.

A problem in this art is how to facilitate handling the syringes and, in particular, how to handle two or more syringes such that they can be operated simultaneously with ease. In this regard, it is often desirable to link the syringe barrels and the syringe plungers to allow the operator to apply the contents in a controlled manner with one hand.

It may also be desirable to provide for operation of a single syringe by using the thumb to obtain more leverage on the end of the plunger.

A further requirement of devices in this art is that the components be inexpensive, easily sterilized, and disposable.

SUMMARY OF THE INVENTION

In accordance with the invention, a one-piece molded plastic handle receives the barrel of a first syringe for securely holding it in a position whereby the user may grip the handle and operate the plunger with the thumb. A clip is also provided for connecting the plunger of a syringe placed in the handle to the plunger of one or more additional syringes.

In use, the outlet ends of the syringes are attached to any of several applicator tips that are commercially available for combining fluids from two or more syringes. Thus, the luer lock tips at the outlet ends of the syringes are secured to the applicator tip while the plungers at the opposite ends are secured to the clip provided by the invention to result in a rigid assembly, with the syringe barrels essentially parallel.

One of the syringes is held in the handle so that the operator can operate the syringes simultaneously with the thumb by grasping the handle and pushing on the clip with the thumb.

The syringes may be of the same size, which would provide a 1:1 mixture ratio of the fluids. Or, the syringes may be of different sizes to provide another desired mixing ratio. For example, if the first syringe has a 10 ml capacity, and a second syringe has a 1 ml capacity, the mixing ratio will be 10:1. Syringes of different sizes are easily accommodated because the handle holds only a single syringe, and the remaining syringes are held to the first by the applicator and the clip. By this construction, different sizes of syringes can be accommodated with a single handle by using a clip specifically designed to engage the plungers of the syringes. The preferred handle includes a cradle sized to receive the barrel of a 10 ml syringe. The cradle is open at the top so the barrel can be snapped into the handle from the top or slid in from either end. The cradle can be a cylinder, which may require an adaptor for receiving barrels of different sizes.

The handle also preferably provides a storage bay for one or more clips, which may be of different sizes or may be redundant in case one is dropped during assembly.

In the preferred embodiment, the handle and the slips are injection-molded polypropylene of a grade that withstands sterilization by irradiation or ethylene oxide gas.

BRIEF DESCRIPTION OF THE DRAWINGS

FIG. 5a is a side view of a handle showing storage of the clips.

FIG. 5b is a perspective of the embodiment of FIG. 5a.

FIG. 6 is a side view of the embodiment shown in FIG. 4b showing an adaptor for accommodating syringes of different sizes.

DETAILED DESCRIPTION OF THE PREFERRED EMBODIMENT

Figure 1:
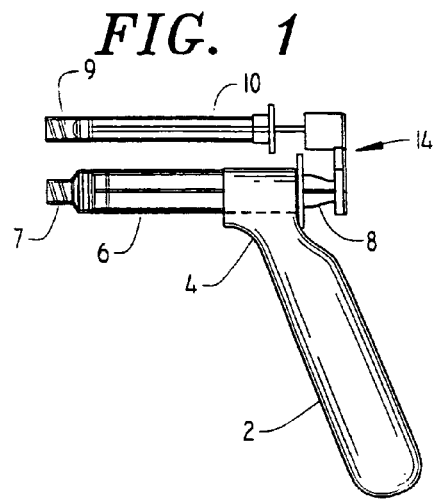
FIG. 1 is a side view of an apparatus for holding one or more syringes in accordance with the invention.

With reference to FIG. 1, a preferred embodiment of the invention includes a handle 2, which is designed with a cradle portion 4 for receiving a first syringe 6. The handle provides a grip for engaging the palm of a user in such a configuration that the thumb of the user is positioned to engage easily the plunger 8 of the syringe 6. A second syringe 10 is held parallel to the first syringe by structure to be described. Each syringe has a luer lock 7 and 9, respectively, for connecting the syringes to conduits, or the like.

Figure 2:
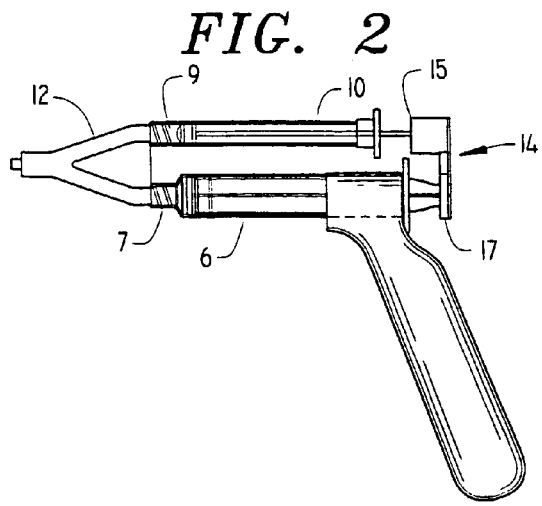
FIG. 2 is a side view of the apparatus of FIG. 1 with an applicator tip attached to the syringes.

With reference to FIG. 2, an applicator tip 12 is shown connected to the luer lock ends of the first and second syringes 6 and 10. This applicator is one of several known in the art for combining the fluids from the first and second syringes to provide a mixture of the fluids from the two syringes. More than two syringes may be employed with an appropriate applicator tip.

Figure 3:
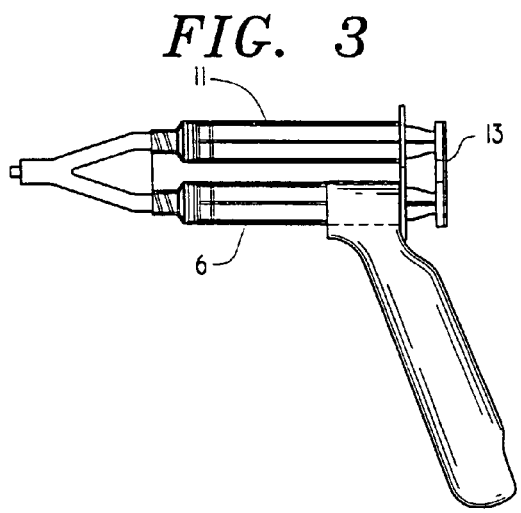
FIG. 3 is a side view of an apparatus in accordance with the invention with an alternate clip.

FIG. 2 also shows use of a clip 14, which is secured to the ends of the syringe plungers such that a user can operate the syringes simultaneously by pressing on the clip 14. The clip 14 can be stepped to provide attachment parts of different thickness to accommodate syringes of different lengths. Thus, the clip shown in FIG. 2 provides a first portion 15 that is thicker than a second portion 17 by the difference between the lengths of the two syringes 6 and 10. FIG. 3 shows an alternate clip 13 of uniform thickness, to be used when the syringes are of the same length.

Figure 4A:
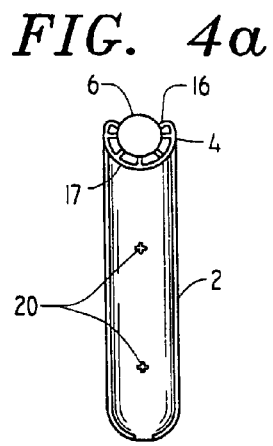
FIG. 4a is an end view of a preferred embodiment of a handle in accordance with the invention.

FIG. 4a is an end view of a handle 2 having a cradle 4 designed to receive a syringe barrel either by insertion from above the cradle in a downward direction or by longitudinally sliding the syringe barrel into the cradle. In this embodiment, the sides 16 of the cradle project inward and downward slightly and are resilient to receive the barrel of a syringe 6 and hold it securely to the handle. Radial ribs 17 are spaced about the cradle 4 for engaging the syringe and providing secure support by the cradle. In this embodiment, the barrel can be inserted in a direction transverse to the longitudinal axis of the barrel or slid longitudinally into the barrel.

Figure 4B:
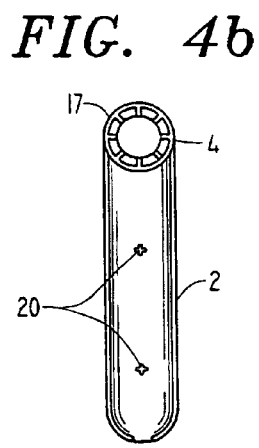
FIG. 4b is an end view of an alternate embodiment of a handle in accordance with the invention.

FIG. 4b shows an alternate embodiment wherein the cradle is designed to receive the barrel only by sliding it longitudinally into the cradle.

FIG. 5a is a side view of the invention showing how spare clips 14 are stored in an open cavity formed by the sides of the handle. In the preferred embodiment, each of the clips has an opening 18 for receiving a post 20 on the handle to hold the clip to the handle such that a user can readily remove the clip from its storage position. The post is preferably cruciform in cross section for resiliently holding the clip.

FIG. 5b is a perspective showing two clips stored in the handle. It will be appreciated that each clip includes front and back walls forming two adjacent slots 24, each of which receives a flange on the end of a respective syringe plunger. The front wall is cut out at 26 to accept the plunger's shaft. The slots are preferably directed oppositely, whereby the plungers are inserted from opposite ends of the clip to accommodate the natural tendency of the syringes to come toward each other.

FIG. 6 shows how a handle, such as that shown in FIG. 4b, can be adapted to receive syringes of different sizes. In this embodiment, an adaptor 22 is provided for altering the size of the cradle to receive a syringe having a diameter smaller than the largest nominal size to be retained by the cradle. A plurality of these adaptors may be provided to accommodate syringes of various sizes.

In use, the syringes may be assembled in almost any order. In one procedure, the applicator tip is secured to the syringes, the syringe 6 is inserted into the cradle 4, and the clip attached. Alternatively, the syringe 6 is inserted into the handle, and the applicator tip, second syringe and clip are then attached. The parts may be assembled in other orders also.

It will be appreciated that a novel for holding and operating one or more syringes has been described. Modifications within the scope of the appended claims will be apparent to those of skill in the art.

What is claimed is:

1. Apparatus for holding and operating one or more syringes each of which has a barrel portion and a plunger, comprising a handle with a portion configured to be gripped in a user's hand and a cradle at one end of said handle, said cradle being configured to removably receive a said barrel portion of a single syringe of said one or more syringes such that it extends transversely to said handle portion and is located such that a said plunger of said single syringe is easily engaged by said user's thumb, and further comprising a clip adapted to engage the ends of the plungers of at least two of said syringes and to connect the plungers for simultaneous movement, wherein said handle provides a cavity for storing one or more of said clips.

2. Apparatus according to claim 1 wherein said clip accommodates syringes of different lengths.

3. Apparatus according to claim 1 wherein each of said at least two syringes has an output end through which an output flows and further comprising an applicator tip for connecting to the output end of each syringe and receiving the outputs from said syringes.

4. Apparatus according to claim 1 wherein said handle includes at least one post for engaging an opening in a said clip.

5. Apparatus according to claim 1 wherein said clip comprises spaced front and rear walls forming grooves to receive said ends of the plungers.

6. Apparatus according to claim 5 wherein one of said walls is cut out to receive a shaft of a syringe plunger.

7. Apparatus according to claim 1 wherein said cradle is semi-cylindrical and is made of resilient material for receiving said barrel portion of said syringe when inserted in a direction toward said handle portion.

8. Apparatus according to claim 1 further comprising an adaptor.

* * * * *